United States Patent [19]

Ripart

[11] Patent Number: 5,776,164
[45] Date of Patent: Jul. 7, 1998

[54] METHOD AND APPARATUS FOR DEFIBRILLATION OF THE ATRIUM

[75] Inventor: Alain Ripart, Gif sur Yvette, France

[73] Assignee: ELA Medical S.A., Montrouge, France

[21] Appl. No.: 729,623

[22] Filed: Oct. 11, 1996

[30] Foreign Application Priority Data

Oct. 13, 1995 [FR] France .................. 95 12052

[51] Int. Cl.⁶ ................................. A61N 1/39
[52] U.S. Cl. ................................. 607/5
[58] Field of Search .................. 607/4, 5, 6, 7, 607/8, 9

[56] References Cited

U.S. PATENT DOCUMENTS

| | | | |
|---|---|---|---|
| 5,207,219 | 5/1993 | Adams et al. | |
| 5,265,600 | 11/1993 | Adams et al. | 607/4 |
| 5,269,298 | 12/1993 | Adams et al. | 607/5 |
| 5,282,836 | 2/1994 | Kreyenhagen et al. | 607/4 |
| 5,411,533 | 5/1995 | Dubreuil et al. | 607/28 |
| 5,462,060 | 10/1995 | Jacobson et al. | 128/702 |

FOREIGN PATENT DOCUMENTS

| | | | |
|---|---|---|---|
| 0 060 117 | 9/1982 | European Pat. Off. | A61N 1/38 |
| 0626182A1 | 11/1994 | European Pat. Off. | A61N 1/368 |
| 92/18198 | 5/1992 | WIPO | |
| 93/02741 | 11/1992 | WIPO | A61N 1/36 |

*Primary Examiner*—Scott M. Getzow
*Attorney, Agent, or Firm*—Orrick, Herrington & Sutcliffe LLP

[57] ABSTRACT

An active implantable medical device of the defibrillator/cardioverter type for the defibrillation or cardioversion of the atrium. The device is able to detect ventricular activity and to deliver conventional low energy ventricular stimulation pulses to the ventricle. It also delivers shock energy pulses having an energy level sufficient to achieve defibrillation and/or cardioversion. The atrial activity is detected to determine the moment at which the shock energy pulse can be delivered to the atrium. The device also recognizes when a ventricular depolarization occurs, and uses this event to control in a conditional manner the delivery of shock energy pulses. More particularly, shock energy pulses are delivered only when the detected ventricular activity indicates the occurrence of a ventricular depolarization following delivery of a ventricular stimulation pulse.

21 Claims, 1 Drawing Sheet

METHOD AND APPARATUS FOR DEFIBRILLATION OF THE ATRIUM

FIELD OF THE INVENTION

The present invention concerns an active implantable medical device and more particularly the class of devices which deliver to the heart electrical impulses of high energy, that is to say pulses of energy that exceed the energy required for the simple stimulation of the heart, which high energy is sufficient to terminate a tachyarrthmia (cardioversion) and/or to cause defibrillation of a cardiac chamber in fibrillation. The high energy pulses are hereinafter referred to as "shock energy pulses" or a "shock", as distinguished from "stimulation" energy pulses. The class of devices includes the so-called "implantable defibrillators" and "devices for cardioversion" or "cardioverters". The present invention also concerns implantable medical devices which are implantable defibrillators/cardioverters/pacemakers as well as implantable defibrillators/pacemakers. It should be understood hereinafter that the term "defibrillation" generally includes cardioversion.

BACKGROUND OF THE INVENTION

A particular class of implantable medical devices functions to deliver an electrical shock energy pulse to the atrium of the patient. These devices always sense or detect the spontaneous electrical activity of the atrium, and, in the case of a detection of an abnormally increased frequency of the atrial rhythm, which is recognized by the device as a fibrillation or very rapid atrial tachycardia, commands the delivery of a shock energy pulse to stop the fibrillation or tachycardia.

One of the known problems in the utilization of these atrial defibrillators is the risk of inducing ventricular fibrillation as a result of the delivery of a shock energy pulse to the atrium. Indeed the applied electrical shock, although directed specifically by leads placed high on the atrial cavity of the heart, can result in an excitation of cells at the level of the ventricle, and produce thereby ventricular fibrillation. This has dramatic adverse consequences on the vital prognosis of the patient.

To avoid a such consequence, it is known to apply the atrial defibrillation shock in synchronization with the ventricular activity, and especially in synchronization with the so-called R wave indicating a depolarization of the ventricle. At such time, the ventricular cells are all refractory and one thus avoids delivering the atrial defibrillation during the vulnerable period of the ventricular activity. The vulnerable period is indicated by the so-called T wave.

U.S. Pat. No. 5,207,219 describes a process to deliver a shock energy pulse for defibrillation/cardioversion in synchronism with the R wave. Once an atrial tachycardia is detected and the decision to defibrillate is taken, the device measures intervals between consecutive R waves so as to determine, and thus to predict, the stability of the ventricular depolarization. A shock will be delivered if the duration between two successive R waves is greater than a determined time interval and is less than an upper limit.

U.S. Pat. No. 5,282,836 describes a process wherein the atrial defibrillation shock is delivered in synchronism with a ventricular stimulation energy pulse, such that the device stimulating the ventricle is set to a frequency that is fixed before the episode of defibrillation.

Nevertheless, these known processes suffer from the disadvantage that they do not insure that a ventricular depolarization has effectively intervened. As recognized by the authors of these two patents, during a fibrillation or very rapid atrial tachycardia, the ventricular rhythm is very unstable, and sometimes very rapid. This can result in a lengthening of the R-T period and thus the proximity of a T wave and the R wave of the following cycle. The wait for stability of the ventricular frequency can be long, and the patient can suffer from this wait. Furthermore, in the case that a ventricular depolarization is not detected or in the case of a detection of noise that can mislead the ventricular detection system, an artificial lengthening between two R waves can result. This, in turn, can result in a false analysis, and therefore, an inappropriate delivery of an atrial defibrillation shock during a non-detected cycle.

OBJECT AND SUMMARY OF INVENTION

It is an object of the present invention to overcome the disadvantages associated with prior techniques, by proposing an implantable medical device for defibrillation of the atrium that provides the delivery of the shock energy pulse and minimizes the likelihood of any induced ventricular fibrillation.

The present invention is broadly directed to an improved implantable medical device of the aforementioned type, that is to say an implantable medical device having the now conventional circuits for delivering a shock energy pulse sufficient for defibrillation and/or cardioversion, for detecting the atrial depolarization activity and determining the moment at which undesired atrial fibrillation and/or tachycardia exists and a shock energy pulse can be delivered to the atrium, for detecting the ventricular activity, and for stimulating the ventricle at a controllable frequency. The reference to delivering a shock energy pulse should be understood to include delivering a cardioversion shock therapy or therapy sequence to revert a tachycardia or a defibrillation shock to revert a fibrillation, as appropriate for the detected atrial condition.

More particularly, according to the invention, the circuit for detecting the ventricular depolarization activity includes ability to recognize the occurrence of a ventricular depolarization and determine when the detected ventricular depolarization follows a delivered ventricular stimulation pulse. This phenomenon is generally referred to as "capture" of the stimulation pulse. As a result, the circuit for delivering the shock energy pulse for defibrillation and/or cardioversion is conditionally controlled to deliver shock energy pulses only when the circuit for detecting the ventricular activity detects the occurrence of a ventricular depolarization following a ventricular stimulation pulse delivered to the ventricle, that is, it confirms capture.

Very advantageously, the circuit for detecting the ventricular depolarization activity preferably comprises, in addition, a processing means for memorizing the ventricular frequency before the moment at which a shock energy pulse can be delivered to the atrium (that is, at the onset of the identified atrial tachycardia or fibrillation), and the circuit for stimulating the ventricle delivers ventricular stimulation pulses at a frequency that is selected to be equal to or greater than the memorized frequency. In this manner the present invention substantially eliminates a possible phenomenon of fusion between a ventricular stimulation pulse and a spontaneous ventricle depolarization.

In accordance with a preferred embodiment of the invention, the processing means for memorizing the ventricular frequency operates to calculate and memorize a sliding window average of the ventricular frequency over a predetermined number of the most recent cycles immediately preceding the onset of an atrial tachycardia, preferably comprised between four and twelve, more preferably eight, cycles. It should be understood that a weighted average of the predetermined number of cycles could be alternatively used. In another embodiment, the frequency of the ventricular stimulation pulses delivered by the circuit delivering the stimulation pulses to the ventricle is advantageously controlled to be an increasing frequency until the presence of a ventricular depolarization following each stimulation impulse is recognized, that is, capture is confirmed. Further, the stimulation frequency can be limited to a predetermined maximum value, preferably 120 beats per minute.

Another aspect of the invention is directed to a method for defibrillating the atrial cavity of a patient using an implantable medical device. One such method comprises the steps of:

(a) sensing atrial depolarizations;

(b) determining whether or not sensed atrial depolarizations occur at a rate corresponding to an atrial tachycardia or fibrillation;

(c) determining whether or not a determined atrial tachycardia or fibrillation exists and is susceptible to be reduced by a shock energy pulse;

(d) in response to step (b) determining that the sensed atrial rate corresponds to an atrial tachycardia or fibrillation:

i) sensing ventricular depolarization activity, ii) stimulating the ventricle, and iii) confirming whether or not there is capture of ventricular depolarization activity in response to a ventricular stimulation; and (e) in response to step (c) determining that the determined atrial tachycardia or fibrillation is susceptible to be reduced by a suitable shock energy pulse and step (d)iii) confirming capture, delivering a shock energy pulse to the atrium. It shall be understood that the shock energy pulse typically has a greater energy to reduce a fibrillation than a tachycardia, as is well known, and an appropriate shock energy pulse (or sequence of pulses) is to be used.

Preferably, step (d)ii) further comprises delivering a sequence of ventricular stimulation pulses and step (e) further comprises confirming capture in a predetermined number of said sequence of stimulation pulses, whereupon the shock energy pulse is thereafter delivered. The sequence of ventricular stimulation pulses may be delivered at an increasing frequency until step (d)iii) confirms capture. The frequency is preferably limited to a maximum frequency, for example, on the order of 120 beats per minute.

The method also may include the step of calculating a ventricular frequency in response to step (c) determining that a determined atrial tachycardia is susceptible to be reduced by a shock energy pulse, wherein step (d)ii) further comprises delivering ventricular stimulation pulses at a frequency that is greater than or equal to the calculated ventricular frequency. The frequency may be calculated as an average of the ventricular frequency over a predetermined number of cycles, for example, the last four to twelve cycles, more preferably the last eight cycles before the onset of the tachycardia or fibrillation.

BRIEF DESCRIPTION OF THE DRAWING

Other characteristics and advantages of the present invention will appear to the person of ordinary skill in the art, in view of the following detailed description, made with reference to the annexed drawing, which is a block diagram of a defibrillator in accordance with a preferred embodiment of the present invention.

DETAILED DESCRIPTION OF THE DRAWING

Figure 1:
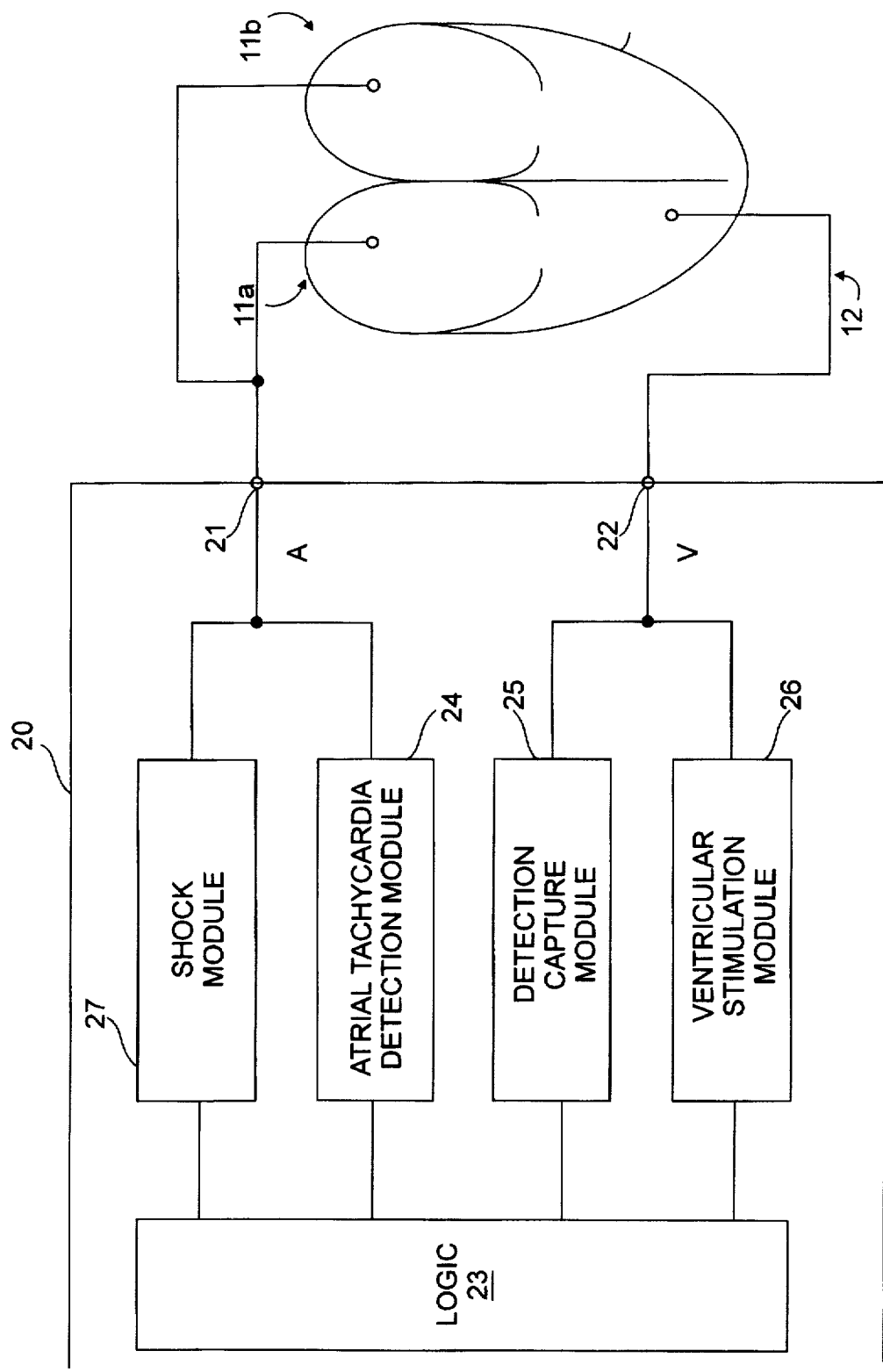

The figure is a block diagram of a defibrillator 20 that can be a typical atrial and ventricular defibrillator with dual chamber sensing capability and composed of a plurality of interdependent circuit modules.

Defibrillator 20 has two in/out terminals 21 and 22. Terminal 21 is connected by the intermediary of leads to left atria 11a and right atria 11b of the heart 10. Terminal 22 is connected by the intermediary of a lead to the right ventricle 12 of the heart 10. These in/out terminals 21 and 22 are capable of collecting (that is sensing or detecting) the electrical activity of each cardiac chamber and to deliver in a known manner cardiac stimulation pulses of low energy to at least the ventricle if not also the atrium, and, if needed, defibrillation and/or cardioversion shocks of high energy.

The present invention can be implemented in a preferred manner with the help of circuits and modules that are employed in the known dual chamber sensing and pacing defibrillators. Such circuits are known from the devices available under the trade names OPUS, CHORUS and DEFENDER manufactured by the company ELA Medical, Montrouge France, the assignee of this invention, to which devices and product literature the reader is directed for further details.

The algorithm of confirmation of the capture can be realized according to teachings of EP-A-0 552 357 and corresponding U.S. Pat. No. 5,411,533, the disclosure of which U.S. Pat. No. 5,411,533 is incorporated herein by reference in its entirety.

It should be understood, however, that any other type of circuit modules, including hard-wired and dedicated discrete logic digital and/or analog circuits, or integrated circuits, can be used to realize the atrial and ventricular depolarization detection (sensing), stimulation (pacing) and shock (cardioversion/defibrillation) functions of the present invention in a manner already known to those skilled in the art. Particular reference is also made to the known implantable dual chamber defibrillator products under the trade name GUIDANT, available from Cardiac Pacemakers Inc., and such products available from Medtronic, Inc. One of ordinary skill in the art will be able to modify the known circuits and/or software, for example, the disclosure of U.S. Pat. No. 5,282,836, which disclosure also is incorporated herein by reference in its entirety, in accordance with the teachings herein, to implement the present invention.

For one useful implementation of the invention, the terminal 21 is connected to a circuit module 24 that detects an atrial tachycardia. In a simplified form of the invention, this circuit module 24 can be a counter of the spontaneous atrial depolarization activity that authenticates the tachycardia (that is, it declares that a tachycardia exists) when the counter reaches a predetermined threshold valve indicating a minimum rate of detected atrial events corresponding to a tachyarrthmia. Additional count thresholds could be used to discriminate between types of tachycardias and fibrillation. Another useful method of detection of the atrial tachycardia is described in EP-A-0 626 182 and the corresponding U.S. Pat. No. 5,462,060, the disclosure of which U.S. Pat. No. 5,462,060 is incorporated herein by reference in its entirety, that is based on the stability of the atrial activity and the stability of the ventricular activity. The time when an atrial tachycardia is known to have begun is also referred to herein as the moment when a shock energy pulse can be delivered to the atrium and the onset of the tachycardia.

The terminal 22 is connected to a circuit module 25 for the detection of ventricular depolarization activity. This circuit module 25 also comprises a circuit structure for confirming capture, that is the ventricular depolarization after delivery of a ventricular stimulation pulse. The functioning of one such module is described in the aforementioned EP-A-0 552 357 and its corresponding U.S. Pat. No. 5,411,533. By the measure of the maximum of the amplitude of the signal collected (sensed) during a window following ventricular stimulation pulse, for example, a window of 64 ms, a ventricular depolarization event can be confirmed as caused by the ventricular stimulation pulse, and results in a confirmed capture.

The defibrillator 20 also comprises a ventricular stimulation circuit module 26, which may be of any type known to a person of ordinary skill in the art, and a logic module 23. In the framework of the present invention, logic module 23 organizes the response of the defibrillator 20 to the different events that are transmitted to it by the previously described circuit modules 24, 25 and 26.

Logic module 23 operates to memorize the ventricular frequency before the occurrence of the atrial tachycardia and to command in an appropriate manner the module 26 to deliver a ventricular stimulation at a frequency that is greater than the frequency previously memorized. This method is known under the name of "overdriving". Stated otherwise, the logic circuit 23 may be configured to shorten progressively the escape interval, cycle to cycle or every n cycles; n being an integer relative to the memorized frequency.

The memorization of the ventricular frequency can be realized by the calculation of a sliding window average of the ventricular rhythm over a predetermined number of cycles, for example, from the last four to sixteen cycles, preferably the last eight cycles.

Stimulation by overdriving can be triggered in successive phases of increasing frequency until a maximal limit in reached, for example, a maximum on the order of 120 beats per minute. For example, if each phase includes "n" successive cycles, then, if during one of these phases, all the ventricular stimulation pulses of the one phase (that is during the "n" successive cycles) are not followed by a confirmation of the capture, then the frequency of stimulation is incremented for the next phase. Thus, the stimulation frequency is increased after each phase until all the ventricular stimulation pulses of a given phase are followed by a detected depolarization of the ventricle or a maximum frequency is reached.

Logic module 23 also operates to control the delivery of the atrial shock energy pulses when the conditions fixed in the control algorithm are satisfied. In this regard, logic module 23 is preferably a microprocessor based device executing software instructions implementing the control algorithm which are stored in firmware or other memory; but the invention also contemplates the use of solid state and dedicated digital and/or analog circuits structured to achieve the same result.

The functioning of the defibrillator 20 according to the present invention can be explained in the following manner. During the beginning of an atrial tachycardia, the module 24 indicates to the module 23 the presence of this tachycardia. By applying the logic or programming of the module 23, module 23 decides that this is an atrial tachycardia or fibrillation that is susceptible to be reduced by a shock.

Concurrent to the detection of the atrial tachycardia or fibrillation, the module 25 measures the activity of the ventricle and confirms to the logic module 23 the occurrence of an R wave of depolarization. The detection of the ventricular depolarization is realized from electro-stimulated complexes by the intermediary of the module 26.

During a first confirmation of a ventricular depolarization that is captured, or when a predetermined number of such captured ventricular depolarizations is confirmed, the device 20 releases an appropriate shock to the atrium. In this manner, the atrial shock will be delivered in synchronism with a ventricular depolarization wave, therefore at a moment where one is confident that the ventricle is not vulnerable to induced fibrillation as a result of the atrial shock.

One skilled in the art will appreciate that the present invention can be practiced by other than the described embodiments, which are presented for purposes of illustration and not of limitation.

I claim:

1. An active implantable medical device for defibrillation or cardioversion of an atrium, comprising:

a shock circuit for delivering a shock energy pulse to the atrium;

an atrial detection circuit operable to detect an atrial depolarization and determine a moment at which said shock energy pulse can be delivered to the atrium;

a ventricular detection circuit operable to detect a ventricular depolarization of a ventricle; and a ventricular stimulation circuit operable to deliver a ventricular stimulation pulse to the ventricle;

wherein the ventricular detection circuit further comprises processing means for recognizing a ventricular depolarization and indicating a ventricular depolarization that is recognized in response to a stimulation pulse, and wherein the shock circuit delivers said shock energy pulse only in response to the ventricular detection circuit indicating the occurrence of a ventricular depolarization in response to the delivery of a ventricular stimulation pulse.

2. The device according to claim 1, which the ventricular detection circuit further comprises processing means for memorizing the ventricular frequency before the determined moment at which a shock energy pulse can be delivered to the atrium, and the ventricular stimulation circuit delivers said ventricular stimulation pulse at a frequency that is greater than or equal to the memorized frequency.

3. The device according to claim 2, in which the processing means operates to calculate and memorize a sliding window average of the ventricular frequency over a predetermined number of cycles preceding the determined moment.

4. The device according to claim 3, in which the sliding window average further comprises an average of between the last four and twelve cycles preceding the determined moment.

5. The device according to claim 3, wherein the sliding window average further comprises an average of the last eight cycles.

6. The device according to claim 1, in which the ventricular stimulation circuit delivers ventricular stimulation pulses at an increasing frequency until said processing means recognizes the presence of a ventricular depolarization following each impulse of stimulation.

7. The device according to claim 6, in which the frequency of stimulation of the ventricle is limited to a predetermined maximum value.

8. The device according to claim 7, which the frequency of stimulation of the ventricle is limited to 120 beats per minute.

9. The device according to claim 1 wherein the atrial detection circuit is operable to identify an atrial rate as an atrial tachycardia, and the shock circuit delivers a shock energy pulse suitable to revert the identified atrial tachycardia.

10. The device of claim 9 wherein the atrial detection circuit is further operable to identify an atrial rate as an atrial fibrillation and the shock delivery circuit delivers a shock energy pulse suitable to defibrillate the identified atrial fibrillation.

11. The device of claim 1 wherein the atrial detection circuit is operable to identify an atrial rate as an atrial fibrillation and the shock delivery circuit delivers a shock energy pulse suitable to defibrillate the identified atrial fibrillation.

12. A method for defibrillating the atrial cavity of a patient using an implantable medical device, comprising the steps of:

(a) sensing atrial depolarizations;
(b) determining whether or not sensed atrial depolarizations occur at a high rate corresponding to one of an atrial tachycardia and an atrial fibrillation;
(c) determining whether or not the determined high atrial rate is susceptible to be reduced by a shock energy pulse;
(d) in response to step (b) determining that the sensed high atrial rate corresponds to one of an atrial tachycardia and an atrial fibrillation:
  i) sensing ventricular activity,
  ii) stimulating the ventricle;
  iii) confirming whether or not there is capture of ventricular activity in response to a ventricular stimulation; and
(e) in response to step (c) determining that the determined high atrial rate is susceptible to be reduced by a shock energy pulse and step (d)iii) confirming capture, delivering a shock energy pulse to the atrium.

13. The method of claim 12 wherein step (d)ii) further comprises delivering a sequence of ventricular stimulation pulses and wherein step (e) further comprises confirming capture in a predetermined number of said sequence of stimulation pulses.

14. The method of claim 12, further comprising calculating a ventricular frequency in response to step (c) determining that a determined high atrial rate is susceptible to be reduced by a shock energy pulse, wherein step (d)ii) further comprises delivering ventricular stimulation pulses at a frequency that is greater than or equal to the calculated frequency.

15. The method of claim 14 wherein calculating the ventricular frequency further comprises calculating an average of the ventricular frequency over a predetermined number of cycles.

16. The method of claim 15 wherein calculating the ventricular frequency further comprises calculating an average of the ventricular frequency over a predetermined number of cycles, the number being selected from between 4 and 12 cycles.

17. The method of claim 14, wherein step (d)ii) further comprises delivering ventricular stimulation pulses at an increasing frequency until step (d)iii) confirms capture.

18. The method of claim 17 wherein step (d)ii) further comprises limiting the delivery of ventricular stimulation pulses to a maximum frequency of 120 beats per minute.

19. The method of claim 12 wherein step (c) further comprises determining that the high atrial rate corresponds to an atrial fibrillation and step (e) further comprises delivering a shock energy pulse sufficient to defibrillate the atrium.

20. The method of claim 19 wherein step (c) further comprises determining that the high atrial rate corresponds to an atrial tachycardia and step (e) further comprises delivering a shock energy pulse sufficient to revert the determined atrial tachycardia.

21. The method of claim 12 wherein step (c) further comprises determining that the high atrial rate corresponds to an atrial tachycardia and step (e) further comprises delivering a shock energy pulse sufficient to revert the determined atrial tachycardia.

* * * * *